(12) United States Patent
Fujita et al.

(10) Patent No.: US 7,262,323 B2
(45) Date of Patent: Aug. 28, 2007

(54) METHOD FOR PRODUCING HIGH PURITY TEREPHTHALIC ACID

(75) Inventors: Hideaki Fujita, Kurashiki (JP); Hiroshi Machida, Kurashiki (JP); Nobuo Namiki, Kurashiki (JP); Yoshio Waguri, Kurashiki (JP)

(73) Assignees: Mitsubishi Gas Chemical Company, Inc., Tokyo (JP); Toyo Boseki Kabushiki Kaisha, Osaki-Shi, Osaka (JP); Mizushima Aroma Company, Ltd., Kurashiki-Shi, Okayama (JP)

( * ) Notice: Subject to any disclaimer, the term of this patent is extended or adjusted under 35 U.S.C. 154(b) by 0 days.

(21) Appl. No.: 10/574,273

(22) PCT Filed: Sep. 30, 2004

(86) PCT No.: PCT/JP2004/014772

§ 371 (c)(1),
(2), (4) Date: Mar. 31, 2006

(87) PCT Pub. No.: WO2005/033058

PCT Pub. Date: Apr. 14, 2005

(65) Prior Publication Data

US 2007/0015935 A1 Jan. 18, 2007

(30) Foreign Application Priority Data

Oct. 2, 2003 (JP) .............................. 2003-344002

(51) Int. Cl.
C07C 51/16 (2006.01)
C07C 17/093 (2006.01)
A61L 9/00 (2006.01)

(52) U.S. Cl. .................... 562/408; 422/31; 570/101

(58) Field of Classification Search .................... None
See application file for complete search history.

(56) References Cited

U.S. PATENT DOCUMENTS 5,008,450 A 4/1991 Yamamoto et al.
5,712,412 A 1/1998 Inary et al.
5,777,161 A 7/1998 Inary

FOREIGN PATENT DOCUMENTS

| JP | 01-160942 | 6/1989 |
| JP | 08-231465 | 9/1996 |
| JP | 09-286758 | 11/1997 |
| JP | 09-286759 | 11/1997 |
| JP | 10-45667 | 2/1998 |
| JP | 2000-191583 | 7/2000 |

Primary Examiner—Thurman K. Page
Assistant Examiner—MLouisa Lao
(74) Attorney, Agent, or Firm—Antonelli, Terry, Stout & Kraus, LLP.

(57) ABSTRACT

A method for producing high purity terephthalic acid wherein a slurry having an acetic acid solvent and, dispersed therein, crude terephthalic acid crystals which has been prepared by subjecting a p-alkyl benzene to a liquid phase oxidation in a solvent of acetic acid is continuously converted to a water slurry by the mother liquid exchange, and then the resultant water slurry is subjected to a hydrogenation treatment, which comprises introducing the above acetic acid slurry to a tower having a center axis having a plurality of agitating blades at the top thereof, to form a region having a high concentration of terephthalic acid crystals in the tower through the sedimentation of the terephthalic acid crystals, supplying the water for substitution to the bottom of the tower in such a manner to form an upward water flow while generating a revolving flow of the high concentration region by the rotation of the agitation blade, to thereby subject said terephthalic acid crystals and said upward water flow to a counter-flow contact, and taking out the acetic acid from a portion being upper than the supply port for the acetic acid slurry while withdrawing the terephthalic acid crystals having contacted with the upward water flow together with the water for substitution from the tower bottom. The above method allows the substitution of the acetic acid solvent of the acetic acid slurry with water, with a high substitution percentage.

2 Claims, 6 Drawing Sheets

METHOD FOR PRODUCING HIGH PURITY TEREPHTHALIC ACID

TECHNICAL FIELD

The present invention relates to a process for producing a high-purity terephthalic acid, and more particularly to a mother liquor displacement in which the mother liquor of an acetic acid slurry containing crude terephthalic acid crystals produced by a liquid-phase oxidation reaction is displaced by water.

BACKGROUND ART

Terephthalic acid is produced by subjecting p-phenylene compounds such as p-alkylbenzenes, typically p-xylene, to a liquid-phase oxidation reaction in an acetic acid solvent in the presence of a catalyst such as cobalt and manganese or in the presence of such a catalyst and an accelerator such as a bromine compound and acetaldehyde. However, the reaction product contains various impurities, such as 4-carboxybenzaldehyde (4CBA) and p-toluic acid, which may cause discoloration. Therefore, higher purification techniques are required to obtain a high-purity terephthalic acid.

There are known various methods for purifying the crude terephthalic acid produced by the liquid-phase oxidation reaction, for example, a method in which the crude terephthalic acid is dissolved in an aqueous solvent at high temperatures and high pressures and the resultant solution is subjected to a catalytic hydrogenation treatment, an oxidation treatment or a recrystallization treatment, and a method in which a slurry of terephthalic acid crystals partially dissolved therein is subjected to a high-temperature immersion treatment. In particular, a method of subjecting a solution of crude terephthalic acid in water to catalytic hydrogenation in the presence of a group VIII noble metal catalyst of the periodic table at high temperatures and high pressures has been utilized for the past several tens years as a large-scale industrial process for the production of high-purity terephthalic acid.

A major problem of the catalytic hydrogenation process is that a large number of steps are required. That is, the catalytic hydrogenation process requires, as the main steps except for complicated and troublesome steps for recovery of catalyst and solvent, a series of equipments including a single- or more-stage oxidation reactor, several sequential crystallizers for rough purification, a separator for rough purification, a dryer for rough purification, a re-dissolution vessel, a catalytic hydrogenation reactor, several sequential crystallizers for fine purification, a separator for fine purification, and a dryer for fine purification.

The major factor to increase the number of steps is the use of acetic acid as the reaction solvent for the production of the crude terephthalic acid by oxidation and the use of water as the solvent for the purification by catalytic hydrogenation. To displace the mother liquor from acetic acid to water, the crude terephthalic acid produced by the oxidation must be once completely separated from the acetic acid solvent, and then dissolved again in water. If the separation of the crude terephthalic acid from acetic acid is incomplete and the crude terephthalic acid with acetic acid attached thereto is fed to the catalytic hydrogenation process, the acetic acid is mixed with water solvent for the catalytic hydrogenation and discharged out of the production system because acetic acid hardly undergoes chemical change during the catalytic hydrogenation. This means a loss of valuable acetic acid, and the discharged acetic acid must be made harmless against the environment, resulting in a large economical loss.

To eliminate the economical loss, it is required to substantially completely prevent the attached acetic acid from accompanying the crude terephthalic acid being fed into the catalytic hydrogenation process. Therefore, in the conventional industrial facilities, a combination of a separator for rough purification and a dryer for rough purification has been employed to separate the mother liquor from the crystal-containing slurry from the oxidation step. A solid bowl-type centrifugal separator or a rotary vacuum filter has been most generally used to separate the mother liquor from a crystal-containing slurry. Both the separators are widely used also in the separation of the mother liquor from the slurry containing the crude terephthalic acid crystals.

In the separation using the solid bowl-type centrifugal separator, an acetic acid slurry is introduced into a basket rotating at a high speed to centrifugally separate the crystals and the mother liquor. The mother liquor is overflowed from a weir provided on the basket, whereas the precipitated crystals are continuously scraped out by a screw. However, this method involves drawbacks of requiring complicated repair and maintenance because of its structural limitations inherent to the centrifugal separator that needs high-speed rotation. In addition, since the crude terephthalic acid crystals are separated in the form of a wet cake containing the mother liquor, an additional drying step must be provided downstream the centrifugal separation step to separate the acetic acid attached to the crude terephthalic acid crystals.

In the separation using the rotary vacuum filter, the crude terephthalic acid crystals placed on the bottom of a housing are sucked onto a cylindrical filter by evacuating the inside of the filter and move upward with the rotation of the filter. Generally, after passing through a washing zone where a rinsing liquid is sprayed over the crude terephthalic acid crystals retained on the filter by suction, the terephthalic acid crystals are separated from the filter as a filter cake. In this method, although the repair and maintenance are relatively easy because a high-speed rotation is not required, it is difficult to completely remove the mother liquor attached to the crude terephthalic acid crystals. Therefore, like the separation using the centrifugal separator, this method also needs a downstream drying step.

To solve the above problems, there have been proposed methods capable of more efficiently removing the mother liquor from the crystals, for example, a method using a separator equipped with a movable filter band (for example, JP 5-65246 A) and a method using a pressure-type rotary filtration separator (for example, JP 6-502653 A). In these methods, since the separated crystals are washed with water to displace the attached mother liquor (acetic acid) by water, a dryer is not required. Although a dryer is not required, these methods require separators of more complicated structure, this making these methods not so advantageous for simplifying the process.

To simplify the process more, it is preferred to separate the crystals from the acetic acid solvent at a temperature close to the oxidation temperature (usually 150 to 230° C.) and feed a slurry of the separated crystals in water into the catalytic hydrogenation step (usually conducted at 250 to 300° C.). This method makes the sequential crystallizer for rough purification in addition to the dryer unnecessary and saves the energy required for cooling and re-heating the crystals and liquids. In addition, since the crystals and the mother liquor are separated at a high temperature, the amount of impurities that precipitate in the crystals from the mother liquor is reduced to increase the quality of the crude terephthalic acid crystals. This leads to another advantage of easy purification.

As a method applicable to such a process, there has been proposed a method in which a crude terephthalic acid is recrystallized from water and the resultant slurry is fed into an upper portion of a vertical column at a high temperature (165° C. or higher), thereby allowing the terephthalic acid crystals to sediment by gravity against a slow upward flow of a high-temperature water to wash away the attached mother liquor (for example, JP 33-5410 B). In this method, the separation of mother liquor is conducted at a high temperature (under pressure) after the terephthalic acid crystals are recrystallized from water. However, this method is basically a mother liquor displacement method for displacing the mother liquor of the terephthalic acid slurry by a fresh solvent.

This mother liquor displacement method is advantageous in that no special powers are required because the crystals are allowed to sediment by gravity, and is attractive because of the simple structure of the apparatus to be used. However, the method is disadvantageous in that the degree of the mother liquor separated from the crystals (hereinafter referred to as "degree of mother liquor displacement") is low, and that experimental results are hardly scaled-up into the practical production. By increasing the speed of upward flow of the high-temperature water, the degree of mother liquor displacement can be increased. However, this requires a large amount of water. In addition, the sedimentation speed of the crystals is decreased by the increase of the speed of upward flow to allow a large amount of small-size crystals to escape from the top of vertical column.

To remove the above drawbacks, there has been proposed a mother liquor displacement method using a vertical column that is horizontally divided by a plurality of partitions with a number of holes to combine a gravitational sedimentation process of the terephthalic acid crystals and a particle transportation process (for example, JP 57-53431 A). The partitions are used to increase the degree of mother liquor displacement by preventing the channeling or back-mixing of the fluid within the apparatus. However, in the mother liquor displacement utilizing the gravitational sedimentation of slurry, the partitions cause the deposition of crystals thereon and clogging and bulking at openings to require much labor for stable operation of the apparatus.

In addition, there has been proposed a displacement column that is horizontally divided by a number of plates. The terephthalic acid crystals are scraped and allowed to fall down through small holes by a scraper blade that are rotated on the plates at a relatively slow speed (for example, JP 1-160942 A). In the working example for displacing the acetic acid solvent for crude terephthalic acid crystals by water using the proposed displacement column, a high degree of mother liquor displacement is achieved, i.e., 99.9% or more of the acetic acid solvent is displaced by water. However, in the apparatus having the fixed plates and the scraper blades rotated at a slow speed (assumed from the examples as about 0.01 m/s by a peripheral speed of the tip end of the blade), the crystals attach to the plates and scraper blades and grow thereon to make the reliability in a long-term operation poor.

DISCLOSURE OF INVENTION

As described above, if the acetic acid solvent of a slurry containing the crude terephthalic acid crystals obtained by liquid-phase oxidation can be removed from the crystals and displaced by water by introducing the slurry into a column apparatus having no complicated physical mechanism at a temperature close to the oxidation temperature, great advantages such as reduction of the number of steps, energy saving and increase of product quality can be attained. However, the conventionally proposed mother liquor displacement methods are still unsatisfactory in the degree of mother liquor displacement, the stable operation and the reliability in a long-term operation.

A first object of the present invention is to provide a process for producing a high-purity terephthalic acid, which is capable of achieving a high degree of mother liquor displacement. The intended degree of mother liquor displacement to be achieved varies depending upon various economical environments of the production plant and not strictly determined, but it is desired to achieve a degree of preferably 98% or more, more preferably a degree of exceeding 99.5%. A second object of the present invention is to provide a process for producing a high-purity terephthalic acid, which is capable of stably maintaining a high degree of mother liquor displacement over a long-term operation.

As a result of extensive researches in view of solving the technical problems in the separation and displacement techniques of the mother liquor in the production of terephthalic acid which have been developed over past several tens years, the inventors have found that a degree of mother liquor displacement as high as 98% or more is stably achieved over a long-term operation by forming a high-concentration zone of terephthalic acid crystals in a column equipped with a central shaft having a plurality of stirring blades along its vertical direction, and by introducing water into the column from a bottom portion thereof to bring the terephthalic acid crystals in the high-concentration zone into counter-current contact with the water while forming circular flows in the high-concentration zone by rotation of the stirring blades. The present invention has been accomplished on the basis of this finding.

Thus, the present invention provides a process for producing a high-purity terephthalic acid, which comprises a mother liquor displacement for continuously converting a slurry of crude terephthalic acid crystals in an acetic acid solvent, which are produced by a liquid-phase oxidation of p-alkylbenzene in the acetic acid solvent, into a slurry in water as a dispersion medium, and a subsequent catalytic hydrogenation of the slurry in water, wherein the mother liquor displacement comprises:

introducing the acetic acid solvent slurry into a column from an upper portion thereof, the column being equipped with a central shaft having a plurality of stirring blades along a vertical direction thereof;

allowing the crude terephthalic acid crystals to sediment to form a high-concentration zone of terephthalic acid crystals in the column;

introducing a displacing water into the column from a bottom portion thereof so as to form an upward flow of water in the column while forming circular flows in the high-concentration zone by rotation of the stirring blades, thereby bringing the terephthalic acid crystals into counter-current contact with the upward flow of water; and discharging the terephthalic acid crystals together with the displacing water from a bottom portion of the column, while simultaneously taking the acetic acid solvent out of a portion of the column which is disposed above a feed portion for introducing the acetic acid solvent slurry.

In the process for producing a high-purity terephthalic acid according to the invention, the acetic acid mother liquor of a slurry of crude terephthalic acid crystals produced by a liquid-phase oxidation is continuously displaced by water in a mother liquor displacement column equipped with a plurality of stirring blades capable of forming circular flows. The process needs no solid-liquid separator and dryer, therefore, the number of steps is reduced to considerably reduced installation costs. Since the mother liquor displacement column used in the invention is easily operated under high-temperature and high-pressure conditions, energies for cooling and re-heating crystals and liquids are saved. In addition, the purification step is easily operated because the content of impurities in the crude terephthalic acid crystals is reduced. Further, the process using the displacement column ensures a stable high degree of mother liquor displacement over a long-term operation and is operated easily. Therefore, by the process of the invention, a high-purity terephthalic acid is produced in industrially extremely advantageous manner.

BEST MODE FOR CARRYING OUT THE INVENTION

Figure 1:
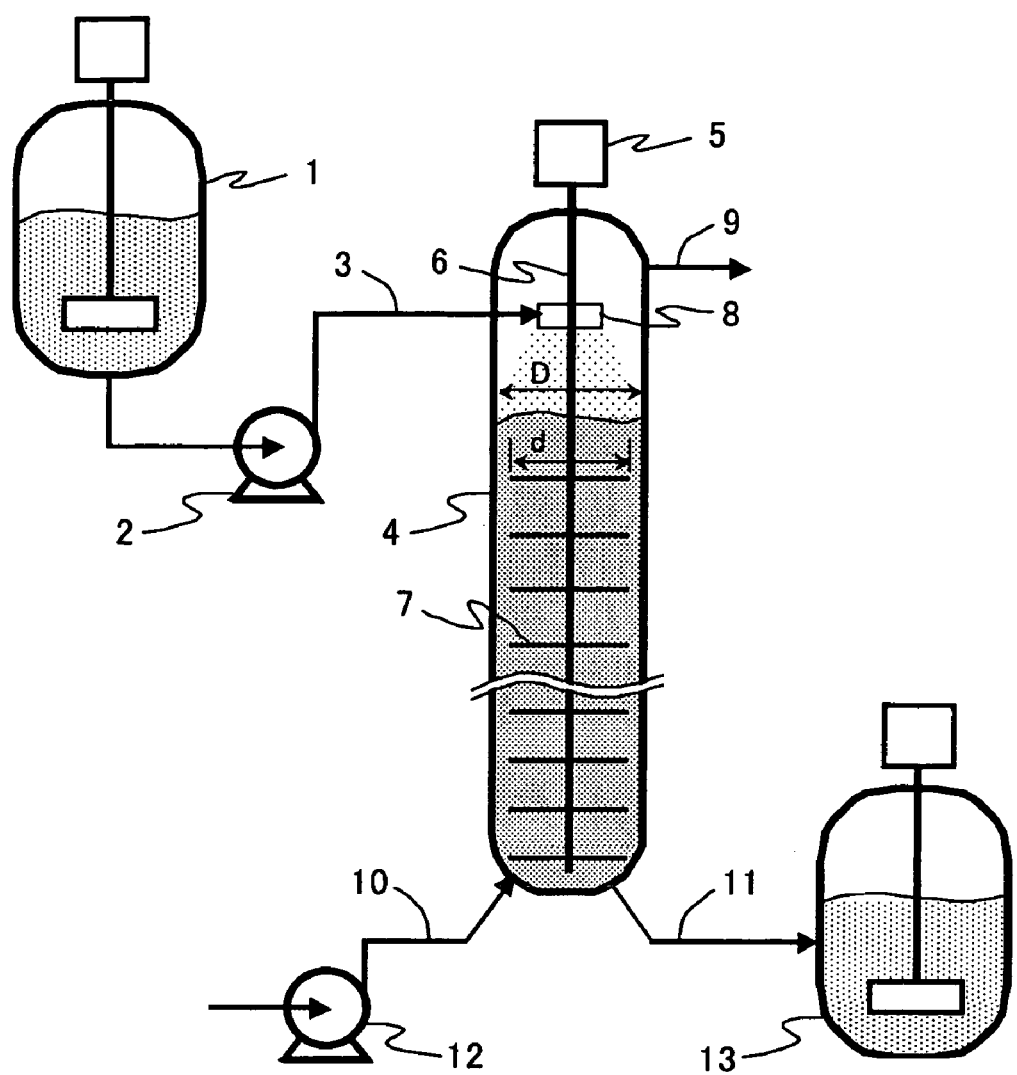
FIG. 1 is a schematic illustration showing the mother liquor displacement apparatus used in Examples 1 to 24.

The slurry of crude terephthalic acid crystals dispersed in an acetic acid solvent (hereinafter occasionally referred to as "acetic acid solvent slurry") which is to be subjected to the mother liquor displacement is produced by oxidizing a p-phenylene compound such as p-alkylbenzene, typically p-xylene, in an acetic acid solvent. The oxidation is usually carried out in the presence of a catalyst of a salt of heavy metal such as cobalt and manganese or in the presence of such a catalyst combined with an accelerator such as a bromine compound and acetaldehyde. Acetic acid containing about 3 to 20% water is used as the solvent. As the oxidizing agent, molecular oxygen, usually air or oxygen is used. The oxidation is usually carried out in single or more stages at 140 to 230° C. under 0.5 to 3 MPa.

The slurry product obtained by the liquid-phase oxidation (i.e., the acetic acid solvent slurry) contains, in addition to the terephthalic acid crystals, 4CBA, p-toluic acid, catalyst and various other impurities. In the conventional process, the acetic acid solvent slurry is introduced into a sequential crystallizer for rough purification of single- or more-stage type, where the slurry is cooled while sequentially reducing the pressure to crystallize the terephthalic acid dissolved in the mother liquor. Then, after reducing the pressure close to atmospheric pressure, the slurry is fed to a separator. During this crystallization step, the impurities dissolved in the mother liquor are crystallized together with the terephthalic acid to increase the concentration of impurities in the terephthalic acid crystals as the temperature is lowered.

Whereas, in the process of the present invention, the acetic acid solvent slurry is fed to the mother liquor displacement column directly or through a deaeration vessel for removing accompanying gas without passing through a step for lowering the temperature in the crystallizer. The higher the temperature of the slurry being fed to the mother liquor displacement column, the higher the sedimentation speed of the crystals in the displacement column, resulting in large throughput per sectional area of the column and the reduction of the concentration of impurities in the terephthalic acid crystals. The temperature of the acetic acid solvent slurry being fed to the displacement column is preferably near the oxidation temperature (generally 150 to 230° C.), i.e., the difference between the oxidation temperature and the feeding temperature is preferably within ±50° C. The acetic acid solvent slurry, in some case, may be fed to the displacement column after heating. However, since the displacement column is required to operate under a higher pressure to prevent the solvent from being evaporated, an excessive heating is disadvantageous.

The crude terephthalic acid crystals fed to the mother liquor displacement column from an upper portion thereof are allowed to gravitationally sediment in the column and discharged from a bottom portion of the column as a slurry in water as a dispersion medium (hereinafter occasionally referred to as "aqueous slurry"). By controlling the amount of the crystals to be discharged from the bottom portion of the column, a high-concentration zone of the crystals is formed in the column. The aqueous slurry of the crude terephthalic acid crystals discharged from the bottom portion of the column is purified by various known methods without additional treatment, for example, by a step for making the aqueous slurry into a solution under high-temperature and high-pressure conditions and a subsequent step of catalytic hydrogenation in the presence of a catalyst of a group VIII noble metal of the periodic table, and finally introduced to a step of separating the high-purity terephthalic acid.

Water for displacing the acetic acid solvent is fed from the bottom portion of the mother liquor displacement column. The displacing water may be fed to two portions, i.e., the inside of the high-concentration zone and a vicinity of the portion for discharging the high-concentration zone. The temperature of the displacing water is preferably the same as or lower than the temperature of the acetic acid solvent slurry to be fed from the upper portion of the column by 100° C. or less. The amount of the displacing water to be fed is controlled to be larger than the water discharged as the aqueous slurry of the crude terephthalic acid crystals so as to form the upward flow of water in the displacement column and allow the crystals being sedimented to come into counter-current contact with the displacing water. The degree of displacement of the acetic acid solvent is increased with increasing velocity of the upward flow of water (upward linear velocity). However, when a superficial upward linear velocity exceeds about 3.3 m/h in the high-concentration zone, the degree of displacement is lowered in some cases. The upward flow of water is mixed with the acetic acid solvent fed at the upper portion of the column and flooded from the overflow port disposed above the feed port for the acetic acid solvent slurry. Therefore, the concentration of water in the acetic acid solvent is increased with increasing upward linear velocity of water flow to increase the energy for removing water from the acetic acid solvent. The lower limit of more than zero is sufficient for the upward linear velocity to form the upward flow of water, and the upper limit is about 3.3 m/h.

Next, the structure and operation conditions of the displacement column which are important to practice the invention are explained. In summary, the mother liquor displacement of the invention is conducted by forming the high-concentration zone of terephthalic acid crystals in a column equipped with a central shaft having a plurality of stirring blades along its vertical direction, and allowing the terephthalic acid crystals to gradually and gravitationally sediment while forming layered, horizontal circular flows in the high-concentration zone by the rotations of the plurality of stirring blades thereby to bring the terephthalic acid crystals into counter-current contact with the displacing water that is fed from the bottom portion of the column.

Figure 2:
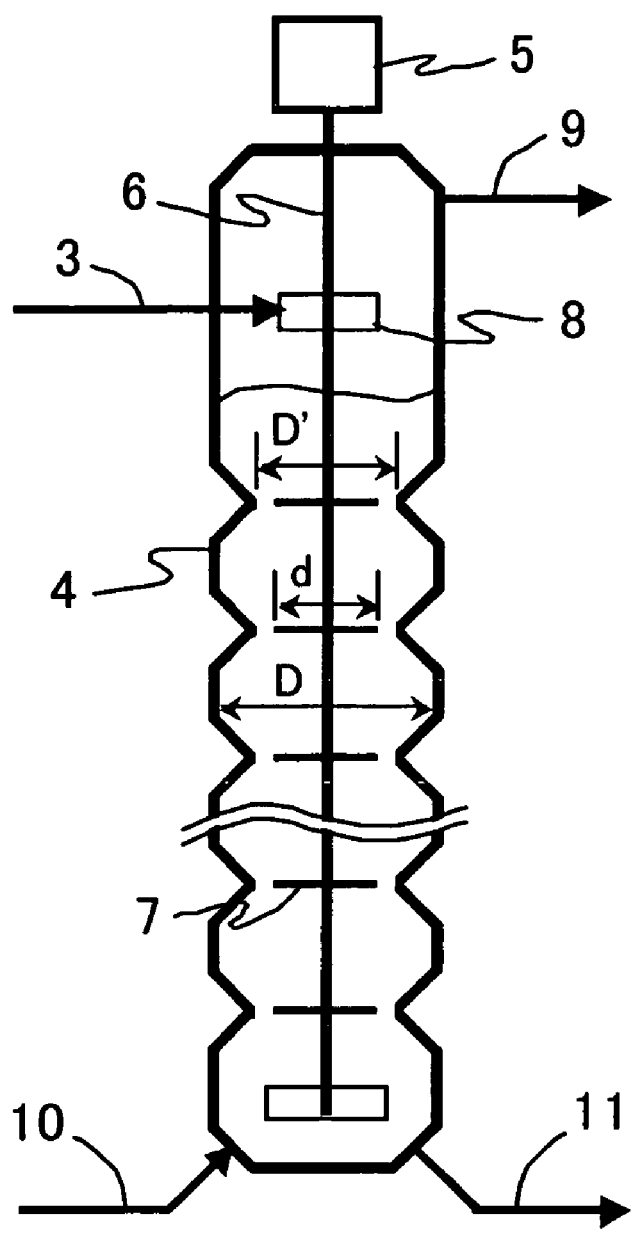
FIG. 2 is a schematic illustration showing the main construction of the mother liquor displacement apparatus used in Example 25.
Figure 3:
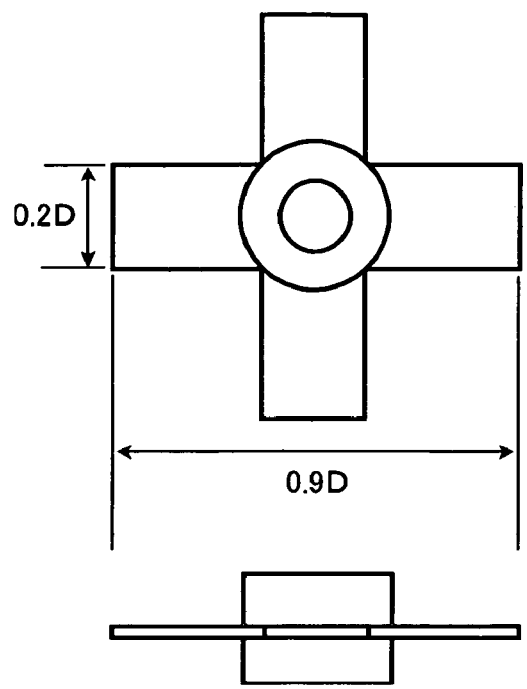
FIGS. 3 to 9 are schematic illustrations showing stirring blades used in the examples. In each figure, the upper is a top plan view and the lower is a side view.

The shape of displacement column is preferably cylindrical. If the horizontal cross section of the column is angular, the circular flows formed by the stirring becomes uneven to make it difficult to achieve a high degree of displacement. The cylindrical shape is preferred also in view of the operation under high pressure to maintain the temperature. As shown in FIG. 2, the column may be radially narrowed at the portions opposing the stirring blades. The shapes of top and bottom of the column are not particularly limited, and generally formed into a flat shape or a semi-elliptical dish shape.

The cylindrical displacement column is provided with a central shaft to which a plurality of stirring blades are fitted along its vertical direction. The stirring blades are disposed at positions capable of stirring the high-concentration zone of the crude terephthalic acid crystals which is formed in the displacement column.

It is preferred to form the high-concentration zone so as to have a height (from the bottom of the displacement column to its upper surface) of 1.03 to 1.5 times the height of the uppermost stirring blade from the bottom of the displacement column.

The stirring should be conducted so as to form the circular flows in the high-concentration zone thereby to intercept channeling in the high-concentration zone and prevent the axial mixing in the high-concentration zone, in addition, to prevent the blocking due to the adhesion of crystals. Therefore, the stirring blades are preferably formed into a shape capable forming flows in the circumferential direction (circular flows) rather than axial flows (flows in up-and-down direction). Examples, but not limited thereto, of such a shape are shown in FIGS. 3 to 6. The slant paddle blade as shown in FIG. 7 is undesirable because it positively forms axial flows. The diameter of the stirring blade is an important shape factor, and should be as large as enough to form circular flows over a whole cross section of the column. The diameter d of the stirring blade is preferably 0.5 to 0.99 and more preferably 0.65 to 0.99 time the inner diameter D of the displacement column. In case of the column as shown in FIG. 2 having radially narrowed portions that oppose the stirring blades, the diameter of the stirring blade is preferably in the above ratio to the inner diameter D' of the narrowed portion.

The number of the stirring blades for attaining the desired degree of mother liquid displacement varies depending upon the throughput of crystals per sectional area of the column and the upward linear velocity of water, and generally 3 or more to obtain a degree of 98% or more displacement and 6 or more to obtain a degree of 99.5% or more displacement.

When the interspace between the stirring blades is too small, flows formed by the adjacent upper and lower stirring blades are interfered or mixed to reduce the degree of mother liquor displacement. Even when the interspace is increased more than needed, no improvement in the displacing capability of the mother liquor per stirring blade is obtained, and instead the overall length of the column is undesirably increased. The preferred interspace of the stirring blades varies depending upon the inner diameter of the displacement column, and 0.3 time or more but less than 3 times the inner diameter D of the displacement column when D is less than one meter, and 0.1 time or more but less than one time the inner diameter D when D exceeds one meter.

The rotating speed of the stirring blade is another important factor having an influence on the degree of mother liquor displacement. If the stirring speed is low, the effect of the circular flows to prevent channeling is reduced to lower the degree of mother liquor displacement and increase the possible deposition of the crystals to the stirring blades. If the stirring speed is too high, the axial mixing in the high-concentration zone becomes dominant to lower the degree of mother liquor displacement. The stirring speed is preferably within the following range:

$$0.10 < v^2/D < 15, \text{ and}$$

more preferably within the following range:

$$0.2 < v^2/D < 6,$$

wherein D is a diameter of the column (m) and v is a peripheral speed of the tip end of the stirring blade (m/s).

In case of the column as shown in FIG. 2 having narrowed portions opposing the stirring blades, the inner diameter D' of the narrowed portions is used in place of D.

The concentration of the slurry in the high-concentration zone (solid concentration in the high-concentration zone by volume basis) varies depending upon the stirring effects, the feeding and discharging amounts of crystals, and the feeding amount of the displacing water. In the production method of the present invention, the degree of mother liquor displacement is reduced by the decrease of the slurry concentration in the high-concentration zone. This is attributable to the convectional mixing of liquid phase because the proportion of liquid phase in the high-concentration zone is increased if the slurry concentration of the high-concentration zone is low. If the slurry concentration is excessively high, the blocking of crystals and the clogging of the outlet for discharging the slurry come to easily occur to make the stable operation difficult. The slurry concentration is preferably 15 to 50% and more preferably 18 to 45% in terms of the average solid concentration by volume basis. The slurry concentration of the high-concentration zone may be controlled by adjusting the ratio between the feeding amount and the discharging amount of the crystals and the feeding amount of the displacing water.

The present invention will be described in more detail by reference to the following examples, but it should be noted that these examples are not intended to limit the scope of the invention thereto.

In the following examples, the degree of mother liquor displacement was calculated from the following formula:

Degree of displacement (%)=[1−(acetic acid flow rate in discharged slurry)/(acetic acid flow rate in feeding slurry)]×100

EXAMPLE 1

Using the apparatus shown in FIG. 1, the displacement of the mother liquor by water was examined on an acetic acid solvent slurry (crude slurry) of crude terephthalic acid crystals obtained by a liquid-phase oxidation. Referring to FIG. 1, the crude slurry stored in a storage tank 1 was fed to an upper portion of a mother liquor replacement column 4 through a feeding pipe 3 with a feeding pump 2. The mother liquor replacement column 4 was constructed by a titanium cylinder having an inner diameter D of 36 mm and equipped with a stirring shaft 6 connected to a motor 5. The stirring shaft 6 was provided with fifteen stirring blades 7 at 50-mm interspaces at its portion below a feed port for the crude slurry. The stirring blades shown in FIG. 3 were used. The diameter d of the stirring blade was 32 mm, being about 9 times the inner diameter D of the column. An outlet pipe 9 for the mother liquor was disposed at the top portion of the mother liquor displacement column 4. At the bottom portion of the mother liquor displacement column, a feeding pipe 10 for the displacing water and a discharging pipe 11 for the displaced slurry were disposed. The displacing water was fed to the mother liquor displacement column 4 by means of a pump 12. In the flow paths 3, 10 and 11, flow meters and flow control valves (not shown) were provided. In the flow path 9, a valve (not shown) for controlling the inner pressure of the column was provided.

In FIG. 1, first, the column was filled with water of 90° C. by driving the pump 12 for feeding water. When water began to overflow from the outlet pipe 9, the feeding amount of water was controlled so as to adjust the upward linear velocity of water flow in the column to 0.5 m/h. Then, the shaft 6 and the stirring blades 7 were rotated at 120 rpm by driving the motor 5. The peripheral speed of the tip end of stirring blade was 0.20 m/s ($v^2/D$=1.1 m/s$^2$).

Next, the feeding pump 2 was operated to feed the crude slurry of 160° C. from a feeding nozzle 8 through the feeding pipe 3 at a flow rate of 8.3 kg/h. The crude slurry used herein was an acetic acid solvent slurry of terephthalic acid which was produced in industrial scale by oxidizing p-xylene at 190° C. in a water-containing acetic acid solvent in the presence of an oxidation catalyst comprising cobalt, manganese and a bromine compound while blowing air into the solvent. The concentration of terephthalic acid crystals in the crude slurry was 30% by weight, and the chemical composition of the mother liquor except for the crystalline component was 86% by weight of acetic acid and 14% by weight of water.

When it was confirmed by the monitor using a powder level detector that the height of the high-concentration zone reached 50 mm above the uppermost stirring blade, the feeding amount of the displacing water was increased and the discharge of the slurry through the bottom of column was started. The displaced slurry discharged from the column was stored in a storage tank 13. The amount of the displaced slurry being discharged from the bottom of column was controlled so as to maintain the height of the high-concentration zone at the intended level, and simultaneously, the amount of the displacing water being fed was controlled so as to maintain the upward linear velocity of water flow in the column at the intended level (0.5 m/h). The operation was continued for 4 h after the system was stabilized, and a sample was taken out of the discharged slurry. The sample was cooled to room temperature, and the crystals were separated from the sample. The concentration of acetic acid in the mother liquor was 0.11% by weight. The calculated degree of acetic acid replacement was 99.91% by weight. After termination of the operation, the slurry remained in the column was discharged to recover the crystals. From the weight of the recovered crystals and the height of the high-concentration zone, the average solid concentration in the high-concentration zone was calculated. The calculated solid concentration was 34% by weight, corresponding to 26% by volume when converted using a specific gravity of terephthalic acid crystals (about 1.5).

EXAMPLE 2

The procedure of Example 1 was repeated except for changing the rotating speed of the stirring blades to 180 rpm (peripheral speed of stirring blade=0.30 m/s; $v^2/D$=2.5). The solid concentration of the high-concentration zone was 25% by volume, and the degree of acetic acid displacement was 99.90% by weight.

EXAMPLE 3

The procedure of Example 1 was repeated except for changing the rotating speed of the stirring blades to 40 rpm (peripheral speed of stirring blade=0.067 m/s; $v^2/D$=0.12). The solid concentration of the high-concentration zone was 27% by volume, and the degree of acetic acid displacement was 98.10% by weight.

EXAMPLE 4

The procedure of Example 1 was repeated except for changing the number of stirring blades to 10 (50-mm interspace). The solid concentration of the high-concentration zone was 26% by volume, and the degree of acetic acid displacement was 99.61% by weight.

EXAMPLE 5

The procedure of Example 1 was repeated except for changing the number of stirring blades to 5 (50-mm interspace). The solid concentration of the high-concentration zone was 26% by volume, and the degree of acetic acid displacement was 98.80% by weight.

EXAMPLE 6

The procedure of Example 1 was repeated except for changing the number of stirring blades to 19 (25-mm interspace). The solid concentration of the high-concentration zone was 26% by volume, and the degree of acetic acid displacement was 99.86% by weight.

EXAMPLE 7

The procedure of Example 1 was repeated except for changing the number of stirring blades to 46 (10-mm interspace). The solid concentration of the high-concentration zone was 25% by volume, and the degree of acetic acid displacement was 98.60% by weight.

EXAMPLE 8

Figure 4:
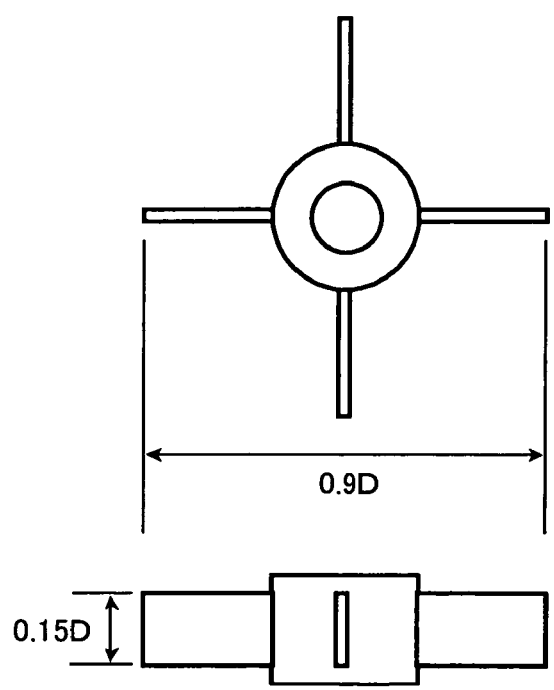

The procedure of Example 1 was repeated except for using the stirring blades as shown in FIG. 4. The solid concentration of the high-concentration zone was 26% by volume, and the degree of acetic acid displacement was 99.11% by weight.

EXAMPLE 9

Figure 5:
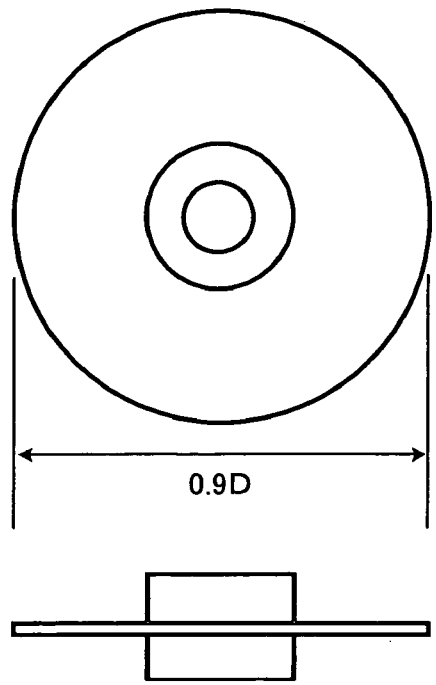

The procedure of Example 1 was repeated except for using the stirring blades as shown in FIG. 5 and changing the peripheral speed of stirring blades to 0.25 m/s. The solid concentration of the high-concentration zone was 26% by volume, and the degree of acetic acid displacement was 99.94% by weight.

EXAMPLE 10

Figure 6:
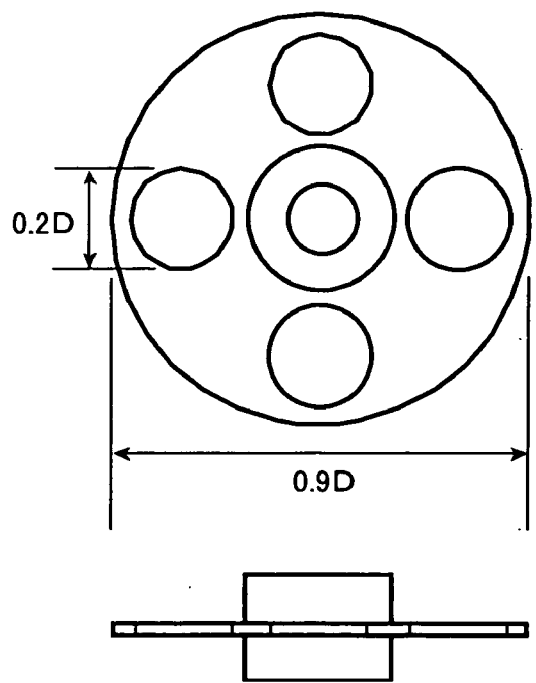
Figure 7:
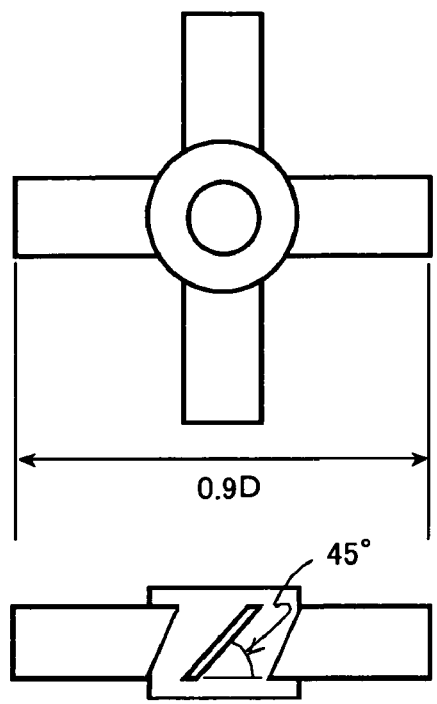

The procedure of Example 9 was repeated except for using the stirring blades as shown in FIG. 6. The solid concentration of the high-concentration zone was 27% by volume, and the degree of acetic acid displacement was 99.93% by weight.

COMPARATIVE EXAMPLE 1

The procedure of Example 1 was repeated except for using the stirring blades (45° slant paddle blades) as shown in FIG. 7. The solid concentration of the high-concentration zone was 26% by volume, and the degree of acetic acid displacement was 95.20% by weight.

EXAMPLE 11

Figure 8:
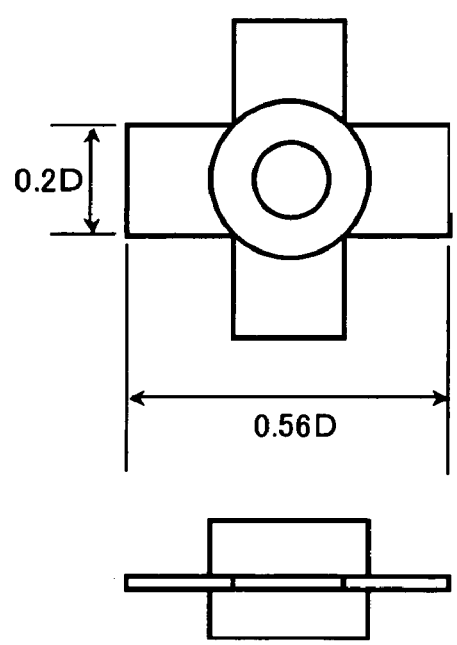

The procedure of Example 1 was repeated except for using the stirring blades (blade diameter: 20 mm (0.56 time the column diameter)) as shown in FIG. 8. The solid concentration of the high-concentration zone was 26% by volume, and the degree of acetic acid displacement was 98.22% by weight.

EXAMPLE 12

Figure 9:
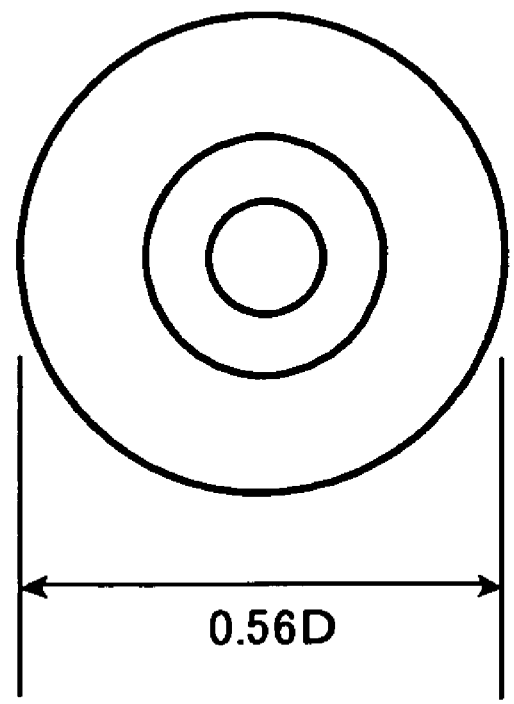
Figure 9:
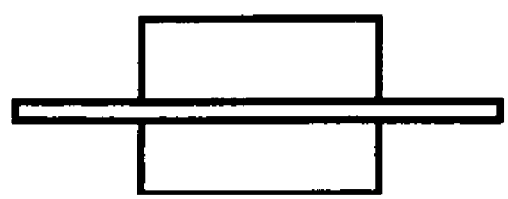

The procedure of Example 9 was repeated except for using the stirring blades (blade diameter: 20 mm (0.56 time the column diameter)) as shown in FIG. 9. The solid concentration of the high-concentration zone was 25% by volume, and the degree of acetic acid displacement was 98.30% by weight.

EXAMPLE 13

The procedure of Example 9 was repeated except for changing the feeding amount of displacing water to 4.3 kg/h. The solid concentration of the high-concentration zone was 31% by volume, and the degree of acetic acid displacement was 99.96% by weight.

COMPARATIVE EXAMPLE 2

The procedure of Example 9 was repeated except for changing the feeding amount of displacing water to 10.3 kg/h. The solid concentration of the high-concentration zone was 13% by volume, and the degree of acetic acid displacement was 97.68% by weight.

EXAMPLE 14

The procedure of Example 9 was repeated except for changing the feeding amount of crude slurry to 12.5 kg/h and the feeding amount of displacing water to 6.5 kg/h. The solid concentration of the high-concentration zone was 27% by volume, and the degree of acetic acid displacement was 99.89% by weight.

COMPARATIVE EXAMPLE 3

The procedure of Example 14 was repeated except for changing the feeding amount of displacing water to 11.0 kg/h. The solid concentration of the high-concentration zone was 14% by volume, and the degree of acetic acid displacement was 97.51% by weight.

EXAMPLE 15

The procedure of Example 9 was repeated except for changing the feeding amount of displacing water to 6.0 kg/h and the upward linear velocity to 1.0 m/h. The solid concentration of the high-concentration zone was 24% by volume, and the degree of acetic acid displacement was 99.93% by weight.

EXAMPLE 16

The procedure of Example 9 was repeated except for changing the feeding amount of displacing water to 8.0 kg/h and the upward linear velocity to 3.2 m/h. The solid concentration of the high-concentration zone was 18% by volume, and the degree of acetic acid displacement was 98.50% by weight.

EXAMPLE 17

Using the displacement column having an inner diameter D of 300 mm equipped with stirring blades having a diameter d of 270 mm, the mother liquor of the acetic acid solvent slurry of terephthalic acid was displaced by water in the same manner as in Example 1. The feeding amount of crude slurry was 520 kg/h, the feeding amount of displacing water was 330 kg/h, and the upward linear velocity was 0.5 m/h. The stirring blades as shown in FIG. 5 were used. The number of stirring blades was 10, and the interspace thereof was 150 mm. The height of the high-concentration zone was maintained 200 mm above the uppermost stirring blade. The peripheral speed of stirring blade was 0.64 m/s ($v^2/D=1.4$). The solid concentration of the high-concentration zone was 26% by volume, and the degree of acetic acid displacement was 99.88% by weight.

EXAMPLE 18

The procedure of Example 17 was repeated except for changing the peripheral speed of stirring blade to 0.20 m/s ($v^2/D=0.13$). The solid concentration of the high-concentration zone was 25% by volume, and the degree of acetic acid displacement was 98.90% by weight.

EXAMPLE 19

The procedure of Example 17 was repeated except for changing the peripheral speed of stirring blade to 1.3 m/s ($v^2/D=5.6$). The solid concentration of the high-concentration zone was 25% by volume, and the degree of acetic acid displacement was 99.35% by weight.

EXAMPLE 20

The procedure of Example 17 was repeated except for changing the peripheral speed of stirring blade to 1.9 m/s ($v^2/D=12$). The solid concentration of the high-concentration zone was 26% by volume, and the degree of acetic acid displacement was 98.10% by weight.

EXAMPLE 21

The procedure of Example 17 was continuously performed for 10 days except for changing the number of stirring blades to 12 (150-mm interspace). The degree of acetic acid displacement calculated from the acetic acid concentration of the slurry discharged from the bottom of column was stable within the range of 99.92 to 99.95% by weight. On the inner inspection of the displacement column after the termination of operation, it was found that the adhesion of crystals to the stirring blades and the inner wall of the column was hardly noticed.

EXAMPLE 22

Using the replacement column as shown in FIG. 2 (in FIGS. 1 and 2, like reference numerals indicate like parts), the procedure of Example 17 was repeated to displace the mother liquor of the acetic acid solvent slurry of terephthalic acid by water. The inner diameter D was 300 mm, and the inner diameter D' of narrowed portions was 200 mm. The stirring blades having a diameter d of 180 mm as shown in FIG. 5 were used. The number thereof was 8 (180-mm interspace). The height of the high-concentration zone was maintained 200 mm above the uppermost stirring blade. The peripheral speed of stirring blade was 0.57 m/s ($v^2/D=1.6$). The solid concentration of the high-concentration zone was 28% by volume, and the degree of acetic acid displacement was 99.93% by weight.

INDUSTRIAL APPLICABILITY

Terephthalic acid produced according to the present invention is useful as a raw material of polyesters for the production of cloths, fibers, bottles, etc.

What is claimed is:

1. A process for producing a high-purity terephthalic acid, which comprises a mother liquor displacement for continuously converting a slurry of crude terephthalic acid crystals in an acetic acid solvent, which are produced by a liquid-phase oxidation of p-alkylbenzene in the acetic acid solvent, into a slurry in water as a dispersion medium, and a subsequent catalytic hydrogenation of the slurry in water, wherein the mother liquor displacement comprises:

introducing the acetic acid solvent slurry into a column from an upper portion thereof, the column being equipped with a central shaft having a plurality of stirring blades along a vertical direction thereof;

allowing the crude terephthalic acid crystals to sediment to form a high-concentration zone of terephthalic acid crystals in the column;

introducing a displacing water into the column from a bottom portion thereof so as to form an upward flow of water in the column while forming circular flows in the high-concentration zone by rotation of the stirring blades, thereby bringing the terephthalic acid crystals into counter-current contact with the upward flow of water; and discharging the terephthalic acid crystals together with the displacing water from a bottom portion of the column, while simultaneously taking the acetic acid solvent out of a portion of the column which is disposed above a feed portion for introducing the acetic acid solvent slurry.

2. The process according to claim 1, wherein an average concentration of solids in the high-concentration zone formed in the column is 15 to 50% by volume.

* * * * *